United States Patent [19]

Ratcliff

[11] Patent Number: 5,348,734
[45] Date of Patent: Sep. 20, 1994

[54] ORAL HEALTH PREPARATION AND METHOD

[75] Inventor: Perry Ratcliff, Scottsdale, Ariz.

[73] Assignee: Micropure Inc., Scottsdale, Ariz.

[21] Appl. No.: 11,401

[22] Filed: Jan. 28, 1993

Related U.S. Application Data

[62] Division of Ser. No. 615,989, Nov. 20, 1990, Pat. No. 5,200,171.

[51] Int. Cl.$^5$ .......................... A61K 7/16; A61K 7/20
[52] U.S. Cl. .......................... 424/53; 424/49; 424/57
[58] Field of Search .......................... 424/53, 57

[56] References Cited

U.S. PATENT DOCUMENTS

| | | |
|---|---|---|
| 2,041,473 | 10/1934 | Janota . |
| 2,191,199 | 2/1940 | Hall . |
| 2,774,672 | 12/1956 | Griffith . |
| 3,123,521 | 3/1964 | Wentworth et al. ............ 167/17 |
| 3,271,242 | 9/1966 | McNicholas et al. ............ 167/17 |
| 3,342,687 | 9/1967 | Gould . |
| 3,577,521 | 5/1971 | Scheller et al. . |
| 3,622,662 | 11/1971 | Roberts . |
| 3,691,272 | 9/1972 | Asche . |
| 3,980,767 | 9/1976 | Chown et al. . |
| 4,044,103 | 8/1977 | Mollard et al. . |
| 4,104,024 | 8/1978 | Vogele et al. . |
| 4,104,190 | 8/1978 | Hartshorn ............ 252/187 |
| 4,132,773 | 1/1979 | Best et al. . |
| 4,198,394 | 4/1980 | Faunce . |
| 4,254,101 | 3/1981 | Denny, Jr. . |
| 4,264,580 | 4/1981 | Barberio . |
| 4,330,531 | 5/1982 | Alliger ............ 424/53 |
| 4,350,680 | 9/1982 | Harvey et al. . |
| 4,515,772 | 5/1985 | Parran, Jr. et al. . |
| 4,542,008 | 9/1985 | Capuano et al. . |
| 4,592,487 | 6/1986 | Simon et al. . |
| 4,684,518 | 8/1987 | Parran, Jr. et al. ............ 424/52 |
| 4,690,772 | 9/1987 | Tell et al. ............ 252/106 |
| 4,721,614 | 1/1988 | Winston et al. ............ 424/52 |
| 4,806,263 | 2/1989 | Leathers et al. . |
| 4,886,657 | 12/1989 | Ratcliff ............ 424/53 |
| 4,889,714 | 12/1989 | Ratcliff ............ 424/53 |
| 4,891,216 | 1/1990 | Kross et al. ............ 424/78 |
| 4,902,498 | 2/1990 | Asricola et al. ............ 424/52 |
| 4,925,656 | 5/1990 | Ratcliff ............ 424/53 |
| 4,975,109 | 12/1990 | Friedman et al. ............ 71/67 |
| 4,986,990 | 1/1991 | Davidson et al. ............ 424/665 |
| 5,009,882 | 4/1991 | Degenhardt et al. ............ 424/52 |
| 5,015,467 | 5/1991 | Smitherman ............ 424/52 |
| 5,019,402 | 5/1991 | Kross et al. ............ 424/665 |
| 5,041,196 | 8/1991 | Cawlfield et al. . |
| 5,041,197 | 8/1991 | Cawlfield et al. ............ 204/101 |
| 5,071,587 | 12/1991 | Perman . |
| 5,084,149 | 1/1992 | Kaczur et al. ............ 204/101 |
| 5,089,095 | 2/1992 | Cawlfield et al. ............ 204/101 |
| 5,092,970 | 3/1992 | Kaczur et al. ............ 204/98 |
| 5,106,465 | 4/1992 | Kaczur et al. ............ 204/98 |
| 5,106,465 | 4/1992 | Kaczur et al. . |
| 5,192,459 | 3/1993 | Tell et al. ............ 252/106 |
| 5,200,171 | 4/1993 | Ratcliff ............ 424/52 |
| 5,217,698 | 6/1993 | Siegel et al. ............ 422/293 |

*Primary Examiner*—Shep K. Rose
*Attorney, Agent, or Firm*—Cahill, Sutton & Thomas

[57] ABSTRACT

A stable mouth wash or dentifrice composition containing stabilized chlorine dioxide and phosphates is disclosed for reducing the motility of and killing microbial pathogens. The preferred concentration ranges are between about 0.005%–0.5% chlorine dioxide, and between about 0.02%–3.0% phosphate. The phosphate retards escape of chlorine dioxide in the pH range (6.0 to 7.4) typically found in a mouth.

15 Claims, No Drawings

ORAL HEALTH PREPARATION AND METHOD

This application is a divisional application of a copending application entitled "ORAL HEALTH PREPARATION AND METHOD", filed Nov. 20, 1990, assigned Ser. No. 07/615,989 now U.S. Pat. No. 5,200,171 and describing an invention by the present inventor.

BACKGROUND OF THE INVENTION

1. Field of the Invention

The present invention is directed to a method and composition for prevention and treatment of gingivitis and periodontitis, as well as dental caries. More particularly, the present invention relates to the use of phosphates in conjunction with stabilized chlorine dioxide to provide a mouth rinse or nonsudsing detergent toothpaste having increased stability and shelf life at a pH which maintains the effectiveness of stabilized chlorine dioxide in reducing the motility of and in killing bacterial pathogens.

2. Description of the Prior Art

The volatile sulfur compounds, hydrogen sulfide ($H_2S$) methylmercaptan ($CH_3SH$) and di-methylmercaptan ($(CH_3)_2S$) are recognized in the current dental literature as being the major contributors to oral malodor. Numerous researchers using organoleptic, chemical, amperometric, mass spectrometric, gas or liquid chromatographic methods have demonstrated that these volatile sulfur compounds are present in the head space and vapor of putrefied saliva and in individual samples of mouth air. In most persons, hydrogen sulfide and methylmercaptan constitute over 90% of the total volatile sulfur content identified in mouth air. Further, the sulfur compounds increase the ability of bacteria and their toxic byproducts to penetrate the lining epethelial barrier of oral mucosa and penetrate into the underlying connective tissue. (Gaffer and Rizzo papers referenced in "Effect of Hydrogen Sulfide and Methyl Mercaptan on the Permeability of Oral Mucosa, J. Dent Res. 63(7), July 1984, pages 994–997).

These malodorous volatile sulfur compounds are generated primarily through the putreficative action of oral microorganisms on sulfur containing amino acids, peptones or proteins found in the mouth. These substrates are readily available in saliva and dental plaque or may be derived from proteinaceous food particles trapped between the teeth, in the gingival crevices or adhering to the mucous membranes and the irregular surface of the tongue as well as exfoliated oral epithelium food debris and the like. Current studies have indicated that mouth odor not only comes from the posterior dorsal surface of the tongue but also from periodontal pockets. People with periodontal involvement have an attendant increase in oral malodor from disintegrated epithelial cells.

Starting with a clean tooth surface, plague formation and resulting ecology occurs in the following steps:

1. Deposition of a coating of glycoproteins from salivary and other oral mucous gland secretions. This is referred to as acquired pellicle.
2. Fastening and colonization of streptococcus organisms to the acquired pellicle primarily by streptococcus sanguis and streptococcus mutans.
3. Conversion of sucrose to glucans (dextran) and fructans by the bacterial enzyme glucosyltransferases. In this plaque mass are imbedded dead cells, cell debris and food debris. High molecular weight polymers of glucose and other sugars, altered salivary glycoproteins, proteases and various chemotactic and inflammatory inducing substances have been detected and partially characterized.
4. Other organisms, primarily gram positive aerobes, become residents in the plaque mass and use the glucans and fructans for nutrition. These are primarily oxygen using organisms and the oxygen source is from the saliva that bathes the plaque mass.
5. With time and the functioning of this ecological system, the oxygen use by the superficial bacteria deprive the lower layers of the plaque matrix of a supply of oxygen. An opportunity is provided for non-oxygen using bacteria (facultative anaerobes) to become established.
6. If left undisturbed, the ecological system now established is self perpetuating. That is, the streptococcus bacteria continue to produce glucans and fructans. Other bacteria product produce toxins that kill cells of the host and the dead cells become other essential nutrients. The superficial bacteria deprive the deeper layers of the plaque mass of oxygen and keep the ecological system going. Thus, both aerobic and anaerobic organisms survive in the plaque mass.
7. The established ecological system attendant the plaque mass produces toxins from the aerobic bacteria that cause gingivitis and toxins from an aerobic bacteria that cause periodontitis.

Various substances have been tested for their ability to disrupt plaque or prevent its formation and to treat mouth odor such as antibiotics, chlorhexidines, oxine, and alexidine.

Over the years, mouth washes and toothpastes have been supplemented with additives which claim to have beneficial effects against dental diseases. For example, fluoride added to toothpaste has been shown to reduce dental caries but has not been shown to prevent gingivitis and periodontal disease. As described in U.S. Pat. No. 4,198,394, the effectiveness of fluoride is reportedly enhanced by adding sodium dihydrogen phosphate to the fluoride containing dentifrice. Phosphate compounds have also been used to stabilize dentifrices, as described in U.S. Pat. Nos. 3,622,662 (dental creams) and 3,577,521 (toothpastes). The prior art compositions that have been used and tested have found some acceptance but are generally ineffective in periodontitis, gingivitis, plaque accumulation and mouth malodor. On the other hand, U.S. Pat. Nos. 4,689,215 and 4,818,519 describe the use of stabilized chlorine dioxide in aqueous solution for the treatment of the mouth as a deodorizing agent, antiplaque agent, bactericide for treatment of gingivitis and periodontitis and as a bactericidal fungicidal and viralcidal agent in other related applications.

Stabilized chlorine dioxide and a method of making it are described in U.S. Pat. No. 3,271,242; stabilized chlorine dioxide is sold by Bio-Cide International, P.O. Box 2700, Norman, Okla., 73070 under the name Purogene. Further discussion of stabilized chlorine dioxide may be found in a treatise entitled "Chlorine Dioxide" by W. J. Masschelein and published by the Ann Arbor Science Publishes, Inc., copyright 1979 (note in particular pages 138–140). Various embodiments of chlorine dioxide for various purposes are also reviewed in this treatise.

Chlorine dioxide, $ClO_2$, functions biochemically in many ways other than as a germicide. These functions include: (1) oxidation of double bonds between two carbon atoms; (2) oxidation of unsaturated fatty acids (lipids) via double bonds between two carbon atoms; (3) acceleration of hydrolysis of carboxalic anhydrides: (4) oxidation of aldehydes to the corresponding carboxylic acids; (5) oxidation of alcohols; (6) oxidation of amines; (7) oxidation of phenols, phenolic derivatives and thiphenolic compounds; (8) moderate oxidation of hydroquinones; (9) oxidation of thiophenols; (10) oxidation of amino acids, proteins and polyamides, primarily by attacking sulphide bonds. These are cystine, methionone and tryosine. Tryptophane also has been shown to be reactive. Keratin, (which makes up the cytoskeletal structure in epithelial cells cytoplasm), and $ClO_2$ keratin sulfonic hydrosoluble acids; (11) carbohydrates are altered as the CHO and $CH_2OH$ radicals to produce carboxylic functions; and (12) Nitrates and sulphides are readily oxidized.

Limited attempts have been made to use chlorine dioxide in toothpaste formulations. For example, U.S. Pat. No. 4,330,530 discloses the topical application of an aqueous gel comprising sodium chlorite simultaneously with the topical application of another aqueous gel compromising lactic acid. Upon mixture of these two gels, non-stabilized chlorine dioxide is produced within the gel mixture. The two gels cannot be premixed without potential loss of an effective application of the operative element (non-stabilized chlorine dioxide). There is no teaching in that reference of the use of stabilized chlorine dioxide.

A relatively new product, Oxyfresh Toothpaste, produced by Oxyfresh USA, Inc. of Spokane, Wash., contains purogene. This formulation uses Sodium Laural Sulphate as a detergent. Inasmuch as $ClO_2$ reacts to sulphates, the $ClO_2$ content is gradually decreased, rendering the formulation inactive with a short shelf life because stabilized chlorine dioxide gas tends to escape from the mixture, the effectiveness and shelf life of the stabilized chlorine dioxide is reportedly accomplished by housing the product in a special aerosol can.

Accordingly, there exists a clear need for a stabilized chlorine dioxide oral health preparation such as a mouth wash and dentifrice such as a toothpaste with an acceptable shelf life which will effectively inhibit the initial pellicle which precedes plaque formation and inhibit or control the formation of bacterial plaque and suppress organisms such as but not limited to (1) "Streptococcus mutans", which is implicated as the major cause of human dental decay; (2) Black Pigmented Bacteriodes, and "Acinobacillus actinomycetumcomitans" which is implied in human periodontitis; and (3) will reduce odor in the mouth through the control of hydrogen and methylmercaptan.

SUMMARY OF THE INVENTION

Briefly, and in accord with one embodiment of the present invention, a composition containing stabilized chlorine dioxide and a phosphate is disclosed as being useful in preventing and treating dental diseases such as gingivitis, periodontitis and dental caries. Stabilized chlorine dioxide is an effective agent for the treatment of the mouth as a deodorizing agent, antiplaque agent, bactericide for treatment of gingivitis and periodontitis and as a bactericidal fungicide and viricidal agent. The addition of activating inhibitor phosphates to the stabilized chlorine dioxide retards the rapid escape of chlorine dioxide gas at the Ph range of 6.5 to 7.0 typical of the mouth. Preferred concentrations of stabilized chlorine dioxide are in the range of between about 0.005% to 0.5%; preferred concentrations of the phosphate, preferably disodium hydrogen phosphate, sodium dihydrogen phosphate, trisodium phosphate, sodium monofluorophosphate, or pyrophosphates are in the range of between about 0.02% to 3.0%.

DESCRIPTION OF THE PREFERRED EMBODIMENT

Broadly, the present invention contemplates the use of an activating inhibitor in a stabilized chlorine dioxide mixture to make possible the lowering of the Ph of the chlorine dioxide mixture at the time it is used in the mouth. Clinical observations by the inventor have led to the discovery that an activating inhibitor phosphate such as disodium hydrogen phosphate, sodium dihydrogen phosphate, or, preferably, trisodium phosphate, will allow the stabilized chlorine dioxide to remain stable and effective at a lower Ph than has been thought possible. In addition, the phosphate is a detergent which, when used in place of the detergent sodium laurel sulfate, provides a nonsudsing toothpaste. Nonsudsing toothpastes are preferred for use with electric toothbrushes because electric toothbrushes tend to spray sudsing toothpastes about the room during use. Further, people tend to quit brushing when a mouth full of suds accumulates in the mouth; a nonsudsing toothpaste does not cause this psychological event.

The first step in the formation of plaque on a clean tooth surface is the formation of acquired pellicle. Studies by others have shown the following to be part of the acquired pellicle formative process. Glycoproteins of salivary and other mucous gland origin are attached to the hydroxyapatite crystals. (Roukima, P. A. and Nieuw Amerongen A. V., Sulphated Glycoproteins in Human Saliva; Saliva and Dental Caries (Sp. Supp. Microbiology Abst.) 1979, pp. 76; Embery, G., The role of anionic glycoconjugates, particularly sulphated glycoproteins in relation to the Oral Cavity, Saliva and Dental Caries. (Supp. Microbiol Abstr.), Information Retrieval 1978, pp. 105–111). Sulphated glycoproteins have a strong affinity to the calcium anion (ibid., pp 105–108). Most major salivary secreted glycoproteins may be bound to certain ester sulphates (ibid). These sulphated glycoproteins have been related to bacterial agglutination or clumping (ibid., pp 108).

Clinical observations by the inventor have led to the discovery that the process of acquired pellicle can be inhibited by the use by humans of stabilized chlorine dioxide. Through such observations it has been learned that the chlorine dioxide reacts with the sulphated glycoproteins to inhibit pellicle formation. This process results primarily from, but is not limited to, oxidation of the sulphide bonds. Since acquired pellicle is the first step in plaque formation, this initial inhibition alters the sequence of events to follow. The second step, bacterial adhesion, and subsequent steps are consequently retarded. No disulphate enzymes capable of cleaning the sulphate moieties of glycoproteins are known.

Bacterial agglutinigation includes the conversion of sucrose to glucans and fructrans by enzymes known as glycosyltransferases. These enzymes are of bacterial origin. The plaque mass becomes a complex extra cellular (of microorganisms) matrix containing sulphated glucosamineglycans, proteglycans, glycoproteins, sugar, proteins and lipids, which aid in the process of bacterial agglutination (Schluger, S., Yuodelis R. and Page R., Periodontal Disease, Chapter 6, pp. 135 to 166, 1977, Lea and Febiger, Phila, Pa. Newbrun E., Polysaccharide Synthesis in Plaque; Microbiol Aspects of Dental Caries, Vol III (Supp. Microbiology Abstr.), 1976, pp 649–664.) These compounds include the presence of sulphur and become unstable in the presence of high oxygen compounds. The oxygen splits the sulphide bonds to form sulphates or $SO_2$.

Clinical observations by the inventor have led to the conclusion that all of these biochemical compounds are attacked to a greater or lesser extent by stabilized chlorine dioxide. Since these compounds may be used as nutrients for bacteria, the reduction of the compounds will inhibit bacterial growth. More specifically, the stabilized chlorine dioxide oxidizes carbohydrates, chondroitin sulphates, glucosaminglycans, glycoproteins, proteins and lipids. Since these compounds arise as bacterial byproducts and debris from dead and dying cells, are of salivary origin and are the mechanism of agglutination of the plaque mass, their degradation/oxidation retards plaque growth.

The initial bacterial residents of the plaque mass are aerobic, oxygen using organisms. The saliva bathing the plaque provides the source of oxygen. As the plaque thickens and the oxygen using bacteria increases in numbers, the deeper layers have a reduced oxygen content. The greater the aerobic population of plaque matrix, the lower the oxygen level in the saliva. This permits the deeper layers of the plaque matrix to develop an anaerobic population of bacteria (Globerman, D. Y., and Kleinberg, I., Intro-Oral $PO_2$ and it's relation to Bacterial Accumulation on the Oral Tissues: saliva and Dental Caries. (Sp. Supp. Microbiology Abstr.) 1976 pp. 275–292).

Clinical observations by the inventor lead to the discovery that the use of stabilized chlorine dioxide with an activating inhibitor in an oral health preparation such as a mouth wash or toothpaste will raise the level of oxygen in the saliva. The raised level of oxygen within the plaque matrix will inhibit anaerobic bacterial growth. As periodontitis is caused by anaerobic bacteria, the potential for the development of periodontitis is reduced by stabilized chlorine dioxide.

The inhibition of acquired pellicle formation, the prevention of bacterial agglutinization and the oxidation of the plaque mass through the use of chlorine dioxide with an activating inhibitor phosphate in a mouth wash or toothpaste are independent of the germicidal capacity of such mouth wash or toothpaste. Furthermore, these factors in combination with the bacteriocidal capacity of chlorine dioxide in the mouth wash or toothpaste renders the mouth wash or toothpaste an effective pellicle and plaque inhibitor.

The permeability of sublingual mucous tissue within the mouth is increased substantially by exposure to hydrogen sulfide ($H_2S$) and methyl mercaptan ($CH_3SH$). (Gaffer and Rizzo papers referenced in "Effect of Hydrogen Sulfide and Methyl Mercaptan on the Permeability of Oral Mucosa, J. Dent Res. 63(7), July 1984, pages 994–997). Accordingly, the toxic bacterial products attendant plaque which produce these compounds have a related effect on tissue permeability. Since chlorine dioxide breaks the disulphide bonds of both these compounds, the use of chlorine dioxide with an activating inhibitor phosphate in a toothpaste would reduce the penetration potential of pathogenic materials. Evidence exists that endotoxin and lipopolysaccharide from gram negative bacteria are the worst of the products to penetrate the tissues. Application of endotoxin to gingiva has caused gingival inflammation. (ibid).

Chlorine dioxide used in treatment of plaque acts upon attendant gram negative bacteria. Thereby, the inventor has learned through experimentation and observation that chlorine dioxide with an activating inhibitor phosphate in a mouth wash or toothpaste can be a preventative product leading to oral health. The use and efficacy of this composition is described below.

EXAMPLE I

The stability of Chlorine Dioxide at Ph 6.8 in the Presence of Phosphate

Materials

1. Purogene (2% $ClO_2$), Lot #8907.41, 1 gallon, Manufactured by BIO-Cide, International, P.O. Box 2700, Norman, Okla. 73070.

2. Sodium Phosphate, monobasic, dibasic, and tribasic.

Methods

A 10% solution of monobasic sodium phosphate was prepared in distilled water. Ten ml was placed into each of four beakers. One of each of the four beakers received 1, 2.5, 5, and 10 ml of chlorine dioxide concentrate (2% $ClO_2$), respectively. All solutions were diluted to 90 ml with distilled water, adjusted to pH 6.8 with 1N NaOH and 1N HCl, diluted to 100 ml and placed in screw cap bottles.

Solutions containing dibasic and tribasic sodium phosphate and a distilled water blank control were prepared in a similar manner.

Chlorine dioxide content and pH was determined for each solution on days 0, 7, 14, 21 and 28 in accordance with Standard Methods for the Examination of Water and Wastewater, 17th edition, 1989.

Results and Summary

As shown in Table 1, the content of chlorine dioxide was stable in all sodium phosphate solutions and distilled water control over the 28 day test period. The pH of all samples ranged from 6.1 to 7.6.

EXAMPLE II

The Stability of Chlorine Dioxide in Various Toothpastes at pH 5.0, 5.5, and 6.0.

Stabilized chlorine dioxide in alkaline solutions is present as sodium chlorite. Acidification of sodium chlorite results in the liberation of chlorine dioxide gas which is very reactive against organic material.

Materials

1. Tartar Control Crest toothpaste, original flavor, lot #9342TK, manufactured by Procter and Gamble, Cincinnati, Ohio, 45202.

2. Aquafresh for Kids Fluoride toothpaste bubblemint flavor, lot M292B, manufactured by Beecham Products, USA, Pittsburgh, Pa., 15230.

3. Generic toothpaste without a detergent (unlabeled), supplied by Perry Ratcliff, DDS, 7125 East Lincoln Drive, Scottsdale, Ariz. 85253.

4. Trisodium phosphate, $Na_3PO_4.12H_2O$. Fisher Scientific, Fair Lawn, N.J.

TABLE 1

RESULTS SHOWING THE STABILITY OF CHLORINE DIOXIDE SOLUTION AT pH 6.8 IN DISTILLED WATER AND 1% SODIUM PHOSPHATE, MONOBASIC, DIBASIC, AND TRIBASIC

| SOLUTION | Theroetical % $ClO_2$ | DAY 0 pH | % $ClO_2$ | 7 pH | % $ClO_2$ | 14 pH | % $ClO_2$ | 21 pH | % $ClO_2$ | 28 pH | % $ClO_2$ |
|---|---|---|---|---|---|---|---|---|---|---|---|
| Distilled Water | 0.02 | 6.8 | 0.02 | 6.9 | 0.02 | 6.9 | 0.02 | 6.5 | 0.02 | 6.5 | 0.02 |
|  | 0.05 | 6.8 | 0.05 | 6.9 | 0.05 | 6.9 | 0.05 | 7.1 | 0.05 | 6.9 | 0.05 |
|  | 0.1 | 6.8 | 0.1 | 6.9 | 0.1 | 7.0 | 0.1 | 7.7 | 0.1 | 7.6 | 0.1 |
|  | 0.2 | 6.8 | 0.2 | 6.9 | 0.2 | 6.9 | 0.2 | 7.2 | 0.2 | 7.2 | 0.2 |
| 1% $Na_2HPO_4$ | 0.02 | 6.8 | 0.02 | 6.1 | 0.02 | 6.7 | 0.02 | 6.7 | 0.02 | 6.8 | 0.02 |
| (Disodium | 0.05 | 6.8 | 0.05 | 6.8 | 0.05 | 6.8 | 0.05 | 6.8 | 0.05 | 6.8 | 0.05 |
| hydrogen phosphate) | 0.1 | 6.8 | 0.1 | 6.9 | 0.1 | 6.9 | 0.1 | 6.8 | 0.1 | 6.8 | 0.1 |
|  | 0.2 | 6.8 | 0.2 | 6.9 | 0.2 | 6.9 | 0.2 | 6.9 | 0.2 | 6.8 | 0.2 |
| 1% $aH_2PO_4$ | 0.02 | 6.8 | 0.02 | 6.7 | 0.02 | 6.8 | 0.02 | 6.7 | 0.02 | 6.8 | 0.02 |
| (Sodium | 0.05 | 6.8 | 0.05 | 6.8 | 0.05 | 6.8 | 0.05 | 6.8 | 0.05 | 6.9 | 0.05 |
| dihydrogen | 0.1 | 6.8 | 0.1 | 6.8 | 0.1 | 6.8 | 0.1 | 6.9 | 0.1 | 6.9 | 0.1 |
| phosphate) | 0.2 | 6.8 | 0.2 | 6.8 | 0.2 | 6.8 | 0.2 | 6.9 | 0.2 | 6.9 | 0.2 |
| 1% $Na_3PO_4$ | 0.02 | 6.8 | 0.02 | 6.8 | 0.02 | 6.4 | 0.02 | 6.9 | 0.02 | 7.0 | 0.02 |
| (Trisodium | 0.05 | 6.8 | 0.05 | 7.0 | 0.05 | 7.1 | 0.05 | 6.9 | 0.05 | 7.0 | 0.05 |
| phosphate) | 0.1 | 6.8 | 0.1 | 7.5 | 0.1 | 7.5 | 0.1 | 7.0 | 0.1 | 6.9 | 0.1 |
|  | 0.2 | 6.8 | 0.2 | 7.0 | 0.2 | 7.1 | 0.2 | 6.9 | 0.2 | 6.9 | 0.2 |

5. Purogene, (2% Chlorine dioxide), lot #8907:41, manufactured by BIO-CIDE International, Inc., P.O. Box 2700, Normal, Okla. 73070.

Methods

Crest and Aquafresh Toothpaste

Each toothpaste was divided into three 50 g portions and placed in plastic jars with lids. One portion of each toothpaste was adjusted to pH 5.0, 5.5, and 6.0, respectively, with 1N NaOH and 1N HCl. Subsequently 5 ml 2% Chlorine dioxide was added to each portion and mixed thoroughly, yielding a chlorine dioxide concentration of approximately 0.15%.

Generic Toothpaste

Toothpaste was dispensed into four jars, 50 g per jar. Jars were divided into groups of two each. Jars in the first group each received 1.2 g $Na_3PO_4.12H_2O$ (1% $Na_3PO_4$) while jars in second group each received 2.3 g $Na_3PO_4.12H_2O$ (2% $Na_3PO_4$). One jar from each group was adjusted to pH5.0 and 6.0, respectively. Subsequently 5 ml 2% Chlorine dioxide was added to each portion and mixed thoroughly, yielding a chlorine dioxide concentration of approximately 0.15%.

The pH and chlorine dioxide content of all jars was determined. Jars were stored in the dark at @ 20 degrees C. and reassayed for pH and chlorine dioxide content on days 7, 14, 21 and 28.

RESULTS AND SUMMARY

As shown in Table 2, the pH values of Crest and generic toothpaste with 1% and 2% trisodium phosphate were stable during the twenty-eight day test period. In sharp contrast, the pH values of Aquafresh toothpaste increased from 0.4 to 1.0 units during the 28 day test period.

Table 3 shows the percentage of chlorine dioxide remaining in the various toothpastes on days 0, 7, 14, 21, and 28.

Chlorine dioxide in Crest toothpaste gradually decreased during the 28 day test period. On day 28, 6% of the original chlorine dioxide was remaining in Crest toothpaste at pH 5.0. In sharp contrast, 54% of the chlorine dioxide was present in Crest toothpaste at pH 6.0, nine fold greater than at pH 5.0.

Chlorine dioxide content in Aqua Fresh toothpaste remained stable for the first 21 days (78–100% of $ClO_2$ remaining) at all Ph levels. A sharp drop in chlorine dioxide concentration occurred on day 28; the reason for the decrease is not clear.

Chlorine dioxide content in generic toothpastes containing 1% and 2% trisodium phosphate at pH 5.0 gradually decreased during the 28 day test period. On the 28th day, 5 to 27% of the chlorine dioxide remained, respectively. In sharp contrast, generic toothpaste containing 1% and 2% trisodium phosphate at pH 6.0 remained relatively stable during the 28 day test period (80 to 100% chlorine dioxide remaining). This is three to 20 fold greater retention of chlorine dioxide than at pH 5.0.

Of all the toothpastes tested, generic toothpaste with either 1% or 2% trisodium phosphate at pH 6.0 appears to be the most compatible with chlorine dioxide.

TABLE 2

RESULTS SHOWING pH VALUES OF TOOTHPASTES DURING THE TWENTY-EIGHT DAY TEST PERIOD

| TOOTHPASTE | DAY 0 | 7 | 14 | 21 | 28 |
|---|---|---|---|---|---|
| Crest | 5.0 | 5.0 | 5.0 | 5.0 | 5.0 |
|  | 5.5 | 5.5 | 5.5 | 5.5 | 5.5 |
|  | 6.0 | 6.0 | 6.0 | 6.0 | 6.0 |
| Aqua Fresh | 5.0 | 5.6 | 5.7 | 5.9 | 6.0 |
|  | 5.5 | 5.7 | 5.7 | 5.8 | 5.9 |
|  | 6.0 | 6.2 | 6.3 | 6.4 | 6.6 |
| Generic w/1% $Na_3PO_4$ | 5.0 | 5.0 | 5.0 | 5.0 | 5.1 |
|  | 6.0 | 6.0 | 6.0 | 6.0 | 6.1 |
| Generic w/2% $Na_3PO_4$ | 5.0 | 5.1 | 5.0 | 5.1 | 5.2 |
|  | 6.0 | 6.0 | 6.0 | 6.0 | 6.1 |

TABLE 3

RESULTS SHOWING THE STABILITY OF CHLORINE DIOXIDE IN TOOTHPASTES AT VARIOUS pH LEVELS DURING TWENTY-EIGHT DAY TEST PERIOD

| TOOTHPASTE | pH* | PERCENT CHLORINE DIOXIDE REMAINING ON DAYS 0 | 7 | 14 | 21 | 28 |
|---|---|---|---|---|---|---|
| Crest | 5.0 | 100 | 56 | 38 | 19 | 6 |
|  | 5.5 | 100 | 60 | 47 | 40 | 27 |
|  | 6.0 | 100 | 85 | 77 | 62 | 54 |
| Aqua Fresh | 5.0 | 100 | 86 | 86 | 93 | 43 |
|  | 5.5 | 100 | 89 | 89 | 78 | 22 |
|  | 6.0 | 100 | 100 | 100 | 100 | 17 |
| Generic w/1% $Na_3PO_4$ | 5.0 | 100 | 55 | 25 | 10 | 5 |
|  | 6.0 | 100 | 100 | 100 | 93 | 80 |
| Generic w/2% | 5.0 | 100 | 73 | 87 | 33 | 27 |

TABLE 3-continued

RESULTS SHOWING THE STABILITY OF CHLORINE DIOXIDE IN TOOTHPASTES AT VARIOUS pH LEVELS DURING TWENTY-EIGHT DAY TEST PERIOD

| TOOTHPASTE | pH* | PERCENT CHLORINE DIOXIDE REMAINING ON DAYS | | | | |
|---|---|---|---|---|---|---|
| | | 0 | 7 | 14 | 21 | 28 |
| $Na_3PO_4$ | 6.0 | 100 | 82 | 82 | 88 | 82 |

*pH Day 0.

EXAMPLE III

The Antimicrobial Effectiveness Of Chlorine Dioxide in Phosphate Solution

Materials

1. Purogene (2% chlorine dioxide), lot #8907:41, manufactured by BIO-CIDE International, Inc., P.O. Box 2700, Norman, Okla. 73070.
2. Test Organisms: Streptococcus mutans (ATCC #27152), Streptococcus sanguis (ATCC #10556), and Candida albicans (ATCC #18804)
3. Saline, 0.9% NaCl.
4. Butterfield's Buffer phosphate dilutent (BFB), pH 7.2.
5. Sterile 15% sodium thiosulfate.
6. Blood agar.
7. Stop watch.
8. Sterile 1N HCl and 1N NaOH.
9. pH meter.
10. McFarland nephelometer tube No. 1. Density of this tube is equivalent to a bacterial suspension of $3 \times 10^8$ organisms per ml.
11. N,N-diethyl-p-phenylenediamine (DPD reagent).
12. Phosphate buffer reagent.
13. Sodium dihydrogen phosphate, $NaH_2PO_4.7H_2O$. (Fisher Scientific, Fair Lawn, N.J.
14. Trisodium phosphate, $Na_3PO_4.12H_2O$. Albright & Wilson, P.O. Box 80, Oldbury, Narley, West Midlands, B694LN, England.
15. Sodium monofluorophosphate, $Na_2FPO_3$, Ref No. OB 12837, manufactured by Albright and Wilson, P.O. Box 80, Oldbury, Narley, West Midlands, B694LN, England.

DPD reagent and phosphate buffer reagent were prepared in accord with Standard Methods for the Examination of Water and Wastewater, 17th Edition, p. 9-54 (1989).

Methods

1. Test Solutions

A ten percent sodium dihydrogen phosphate solution was prepared in distilled water. Ten ml was placed into each of five beakers. One of each of the five beakers received 0, 1, 2.5, 5, and 10 ml of chlorine dioxide concentrate (2% $ClO_2$), respectively. All solutions were diluted to 90 ml with distilled water, adjusted to pH 6.0 with 1N NaOH and 1N HCl, diluted to 100 ml and placed in screw cap bottles. Solutions containing 0 ppm chlorine dioxide were filter sterilized prior to use.

Solutions containing trisodium phosphate and sodium monofluorophosphate were prepared in a similar manner.

II. Test Suspensions

Suspensions of each organism were prepared in Butterfield's buffer from 48 hour agar cultures and turbidity adjusted to a McFarland Tube #1. Subsequently 0.1 ml of this suspension was diluted in 50 ml of saline. The diluted microorganism suspensions were now ready for use.

III. Test Procedure

1. Test:

One ml of test suspension was aliquoted into each of five sterile 16×125 mm screw cap tubes. Each of the five tubes received 4 ml of a solution containing either 0, 200, 500, 1000, or 2000 ppm chlorine dioxide in 1% sodium dihydrogen phosphate. Each tube was shaken for ten seconds and immediately inactivated with 0.25 ml 15% sodium thiosulfate. Solutions containing 1% trisodium phosphate and 1% sodium monofluorophosphate were handled in a similar manner.

2. Controls:

One ml of test suspension was dispensed into two sterile 16×125 mm screw cap tubes. Each tube received 4 ml 2000 ppm chlorine dioxide in 1% sodium dihydrogen phosphate. The first tube received 0.25 ml sodium thiosulfate, while the second tube received none. Subsequently each tube was tested for residual chlorine dioxide by adding 0.3 ml phosphate buffer reagent and 0.3 ml DPD reagent to each tube. Neutralized tubes were colorless, while nonneutralized tubes were pink. Solutions of trisodium phosphate and sodium monofluorophosphate containing 2,000 ppm chlorine dioxide were handled in a similar manner.

One ml test suspension of each organism was treated with 4 ml Butterfield's buffer and 0.25 ml 10% sodium thiosulfate as a negative control.

After inactivation with sodium thiosulfate all tubes were plate counted.

Sterility tests on all reagents were run parallel to experiments by plate counted method. The plate counted method and sterility tests were conducted in accord with Standard Methods for the Examination of Water and Wastewater, 17th Edition, p. 9-54 (1989).

RESULTS AND SUMMARY

As shown in Tables 4, 5 and 6, 99-100% of the organisms were killed when challenged with 2,000 ppm (0.2%) chlorine dioxide in either 1% sodium dihydrogen phosphate or trisodium phosphate. In sharp contrast, only fifty percent of S.mutans were killed when challenged with 2,000 ppm chlorine dioxide in sodium monofluorophosphate.

S.sanguis and C.albicans were 99-100% killed when challenged with 1,000 ppm (0.1%) chlorine dioxide in either 1% sodium dihydrogen phosphate or trisodium phosphate. In sharp contrast, S.mutans was killed 24 and 76%, respectively, when similarly challenged. 1,000 ppm chlorine dioxide in 1% sodium monofluorophosphate yielded a 12% kill when used against S. mutans.

Chlorine dioxide concentrations of 200 (0.02%) and 500 ppm (0.05%) in the presence of phosphates demonstrated marginal bacteriocidal activity against S.mutans, S.sanguis, and C.albicans (6-66% kill).

TABLE 4

RESULTS SHOWING THE BACTERIOCIDAL ACTIVITY OF CHLORINE DIOXIDE IN PHOSPHATE SOLUTIONS AT pH 6.0 AGAINST STREPTOCOCCUS MUTANS.

| $CLO_2$ (PPM) | Negative Control* | PHOSPHATE SOLUTION | | |
|---|---|---|---|---|
| | | $NaH_2HPO_4$ | $Na_3PO_4$ | $Na_2FPO_3$ |
| 0 | 17,000** | 16,000 (6)*** | 18,000 (0) | 14,000 (18) |
| 200 | ND | 15,000 (12) | 16,000 (6) | 14,000 (18) |
| 500 | ND | 15,000 (12) | 15,000 (12) | 14,000 (18) |
| 1000 | ND | 13,000 (24) | 4,100 (76) | 15,000 (12) |

TABLE 4-continued

RESULTS SHOWING THE BACTERIOCIDAL ACTIVITY OF CHLORINE DIOXIDE IN PHOSPHATE SOLUTIONS AT pH 6.0 AGAINST STREPTOCOCCUS MUTANS.

| $ClO_2$ (PPM) | Negative Control* | PHOSPHATE SOLUTION | | |
|---|---|---|---|---|
| | | $NaH_2PO_4$ | $Na_3PO_4$ | $Na_2FPO_3$ |
| 2000 | ND | 2 (99) | 120 (99) | 8,500 (50) |

*Butterfield's Buffer
**Organisms/ml
***Percent Kill
ND = Not Done

TABLE 5

RESULTS SHOWING THE BACTERIOCIDAL ACTIVITY OF CHLORINE DIOXIDE IN PHOSPHATE SOLUTIONS AT pH 6.0 AGAINST STREPTOCOCCUS SANGUIS

| $ClO_2$ (PPM) | Negative Control* | PHOSPHATE SOLUTION | |
|---|---|---|---|
| | | 1% $NaH_2PO_4$ | 1% $Na_3PO_4$ |
| 0 | 29,000** | 22,000 (24)*** | 25,000 (14) |
| 200 | ND | 22,000 (24) | 19,000 (34) |
| 500 | ND | 16,000 (45) | 11,000 (62) |
| 1000 | ND | 360 (99) | 0 (100) |
| 2000 | ND | 0 (100) | 0 (100) |

*Butterfield's Buffer
**Organisms/ml
***Percent Kill
ND = Not Done

TABLE 6

RESULTS SHOWING THE BACTERIOCIDAL ACTIVITY OF CHLORINE DIOXIDE IN PHOSPHATE SOLUTIONS AT pH 6.0 AGAINST CANDIDA ALBICANS

| $ClO_2$ (PPM) | Negative Control* | PHOSPHATE SOLUTION | |
|---|---|---|---|
| | | 1% $NaH_2PO_4$ | 1% $Na_3PO_4$ |
| 0 | 95,000** | 64,000 (33)*** | 55,000 (42) |
| 200 | ND | 58,000 (39) | 64,000 (33) |
| 500 | ND | 47,000 (51) | 32,000 (66) |
| 1000 | ND | 250 (99) | 0 (100) |
| 2000 | ND | 17 (99) | 5 (99) |

*Butterfield's Buffer
**Organisms/ml
***Percent Kill
ND = Not Done

EXAMPLE IV

The stability of Chlorine Dioxide at Ph 6.8 in the Presence of 0.02% Phosphate

The following is an example of how to test the stability of chlorine dioxide at Ph 6.8 in the presence of 0.02% phosphate.

Materials

1. Purogene (2% $ClO_2$), Lot #8907.41, 1 gallon, Manufactured by BIO-Cide, International, P.O. Box 2700, Norman, Okla. 73070.

2. Sodium Phosphate, monobasic, dibasic, and tribasic.

Methods

A 0.2% solution of monobasic sodium phosphate is prepared in distilled water. Ten ml is placed into each of four beakers. One of each of the four beakers receives 1, 2.5, 5, and 10 ml of chlorine dioxide concentrate (2% $ClO_2$), respectively. All solutions are diluted to 90 ml with distilled water, adjusted to pH 6.8 with 1N NaOH and 1N HCl, diluted to 100 ml and placed in screw cap bottles.

Solutions containing dibasic and tribasic sodium phosphate and a distilled water blank control are prepared in a similar manner.

Chlorine dioxide content and pH is determined for each solution on days 0, 7, 14, 21 and 28 in accordance with Standard Methods for the Examination of Water and Wastewater, 17th edition, 1989, in order to determine the stability of chlorine dioxide over time.

EXAMPLE V

The Stability of Chlorine Dioxide in Various Toothpastes having a 0.02% and 0.05% $Na_3PO_4$ at pH 5.0, 5.5, and 6.0

The following is an example of how to test the stability of chlorine dioxide in various toothpastes having either 0.02% or 0.05% $Na_3PO_4$.

Stabilized chlorine dioxide in alkaline solutions is present as sodium chlorite. Acidification of sodium chlorite results in the liberation of chlorine dioxide gas which is very reactive against organic material.

Materials

1. Tartar Control Crest toothpaste, original flavor, lot #9342TK, manufactured by Procter and Gamble, Cincinnati, Ohio, 45202.

2. Aquafresh for Kids Fluoride toothpaste bublemint flavor, lot M292B, manufactured by Beecham Products, USA, Pittsburgh, Pa., 15230.

3. Generic toothpaste without a detergent (unlabeled), supplied by Perry Ratcliff, DDS, 7125 East Lincoln Drive, Scottsdale, Ariz. 85253.

4. Trisodium phosphate, $Na_3PO_4.12H_2O$. Fisher Scientific, Fair Lawn, N.J.

5. Purogene, (2% Chlorine dioxide), lot #8907:41, manufactured by BIO-CIDE International, Inc., P.O. Box 2700, Norman, Okla. 73070.

Methods

Crest and Aquafresh Toothpaste

Each toothpaste is divided into three 50 g portions and placed in plastic jars with lids. One portion of each toothpaste is adjusted to pH 5.0, 5.5, and 6.0, respectively, with 1N NaOH and 1N HCl. Subsequently 5 ml 2% Chlorine dioxide is added to each portion and mixed thoroughly to yield a chlorine dioxide concentration of approximately 0.15%.

Generic Toothpaste

Toothpaste is dispensed into four jars, 50 g per jar. The jars are divided into groups of two each. Jars in the first group each receive 0.24 $Na_3PO_4$. $12H_2O$ (0.02 $Na_3PO_4$) while jars in second group each receive 0.6 g $Na_3PO_4$. $12H_2O$ (0.05% $Na_3PO_4$). One jar from each group is adjusted to pH5.0 and 6.0, respectively. Subsequently a sufficient amount of 2% Chlorine dioxide is added to each portion and mixed thoroughly to yield a chlorine dioxide concentration of approximately 0.15%.

The pH and chlorine dioxide content of all jars is determined. The jars are stored in the dark at @ 20 degrees C. and reassayed for pH and chlorine dioxide content on days 7, 14, 21 and 28, in order to determine the stability of the various toothpastes.

EXAMPLE VI

The Antimicrobial Effectiveness of Chlorine Dioxide in 0.02% Phosphate Solution

The following is an example of how to test the antimicrobial effectiveness of chlorine dioxide in 0.02% phosphate solution.

Materials

1. Purogene (2% chlorine dioxide), lot #8907:41, manufactured by BIO-CIDE International, Inc., P.O. Box 2700, Norman, Okla. 73070.
2. Test Organisms: Streptococcus mutans (ATCC #27152), Streptococcus sanguis (ATCC #10556), and Candida albicans (ATCC #18804)
3. Saline, 0.9% NaCl.
4. Butterfield's Buffer phosphate dilutent (BFB), pH 7.2.
5. Sterile 15% sodium thiosulfate.
6. Blood agar.
7. Stop watch.
8. Sterile 1N HCl and 1N NaOH.
9. pH meter.
10. McFarland nephelometer tube No. 1. Density of this tube is equivalent to a bacterial suspension of $3 \times 10^8$ organisms per ml.
11. N,N-diethyl-p-phenylenediamine (DPD reagent).
12. Phosphate buffer reagent.
13. Sodium dihydrogen phosphate, $NaH_2PO_4.7H_2O$. (Fisher Scientific, Fair Lawn, N.J.
14. Trisodium phosphate, $Na_3PO_4.12H_2O$. Albright & Wilson, P.O. Box 80, Oldbury, Narley, West Midlands, B694LN, England.
15. Sodium monofluorophosphate, $Na_2FPO_3$, Ref No. OB 12837, manufactured by Albright and Wilson, P.O. Box 80, Oldbury, Narley, West Midlands, B694LN, England.

DPD reagent and phosphate buffer reagent is prepared in accord with Standard Methods for the Examination of Water and Wastewater, 17th Edition, p. 9–54 (1989).

Methods

1. Test Solutions

A 0.2 percent sodium dihydrogen phosphate solution is prepared in distilled water. Ten ml is placed into each of five beakers. One of each of the five beakers receives 0, 1, 2.5, 5, and 10 ml of chlorine dioxide concentrate (2% $ClO_2$), respectively. All solutions are diluted to 90 ml with distilled water, adjusted to pH 6.0 with 1N NaOH and 1N HCl, diluted to 100 ml and placed in screw cap bottles. Solutions containing 0 ppm chlorine dioxide are filter sterilized prior to use.

Solutions containing trisodium phosphate and sodium monofluorophosphate are prepared in a similar manner.

II. Test Suspensions

Suspensions of each organism are prepared in Butterfield's buffer from 48 hour agar cultures and turbidity adjusted to a McFarland Tube #1. Subsequently 0.1 ml of this suspension is diluted in 50 ml of saline. The diluted microorganism suspensions are then ready for use.

III. Test Procedure

1. Test:

One ml of test suspension is aliquoted into each of five sterile 16×125 mm screw cap tubes. Each of the five tubes receives 4 ml of a solution containing either 0, 200, 500, 1000, or 2000 ppm chlorine dioxide in 1% sodium dihydrogen phosphate. Each tube is shaken for ten seconds and immediately inactivated with 0.25 ml 15% sodium thiosulfate. Solutions containing 1% trisodium phosphate and 1% sodium monofluorophosphate are handled in a similar manner.

2. Controls:

One ml of test suspension is dispensed into two sterile 16×125 mm screw cap tubes. Each tube receives 4 ml 2000 ppm chlorine dioxide in 0.02% sodium dihydrogen phosphate. The first tube receives 0.25 ml sodium thiosulfate, while the second tube receives none. Subsequently each tube is tested for residual chlorine dioxide by adding 0.3 ml phosphate buffer reagent and 0.3 ml DPD reagent to each tube. Neutralized tubes are colorless, while nonneutralized tubes are pink. Solutions of trisodium phosphate and sodium monofluorophosphate containing 2,000 ppm chlorine dioxide are handled in a similar manner.

One ml test suspension of each organism is treated with 4 ml Butterfield's buffer and 0.25 ml 10% sodium thiosulfate as a negative control.

After inactivation with sodium thiosulfate all tubes are plate counted.

Sterility tests on all reagents are run parallel to experiments by plate counted method. The plate counted method and sterility tests are conducted in accord with Standard Methods for the Examination of Water and Wastewater, 17th Edition, p. 9–54 (1989), in order to determine the antimicrobial effectiveness of chlorine dioxide in 0.02% phosphate solution.

It will be seen from the foregoing that the mixture of stabilized chlorine dioxide and phosphates as part of a mouth wash or toothpaste has an improved shelf life, and is effective as a bactericide superior to other compositions used today. Both stabilized chlorine dioxide, and phosphates, have been used for many years in other areas and extensive study in animals and in man have demonstrated the compounds' low toxicity and safety.

It will be obvious that various changes, alterations and modifications to the method and process described herein may be made, to the extent that such changes, alterations and modifications do not depart from the spirit and scope of the appended claims therein intended to be encompassed herein.

I claim:

1. A composition for preventing and treating dental disease by reducing the number of micro-organisms in the mouth, said composition comprising a non sudsing dentifrice, wherein the dentifrice contains stabilized chlorine dioxide in the concentration range of between about 0.005%–0.5% and a phosphate compound selected from the group consisting of disodium hydrogen phosphate, sodium dihydrogen phosphate, and trisodium phosphate in a concentration in the range of between about 0.02%–3.0% to retard escape of chlorine dioxide from said composition at a pH in the range of 6.0 to 7.4, thereby increasing the shelf life and efficacy of said composition.

2. The composition as set forth in claim 1, wherein the concentration of stabilized chlorine dioxide is approximately 0.2% and the concentration of phosphate is approximately 1.0%.

3. A composition for preventing and treating dental disease by reducing the number of bacteria in the mouth, said composition comprising a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard escape of chlorine dioxide from said composition at a pH in the range of 6.0 to 7.4, thereby increasing the shelf life and efficacy of said composition.

4. A composition for preventing and treating dental disease by reducing the number of streptococcus mutans bacteria in the mouth, said composition comprising a non sudsing dentifrice, wherein the dentifrice contains stabilized chlorine dioxide in a concentration range of between about 0.005%–0.5% and a phosphate compound selected from the group consisting of disodium hydrogen phosphate, sodium dihydrogen phosphate, and trisodium phosphate in a concentration in the range of between about 0.02%–3.0% to retard escape of chlorine dioxide from said composition at a pH in the range of 6.0 to 7.4, thereby increasing the shelf life and efficacy of said composition.

5. A composition for preventing and treating dental disease by reducing the number of streptococcus mutans bacteria in the mouth, said composition comprising a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard escape of chlorine dioxide from said composition at a pH in the range of 6.0 to 7.4, thereby increasing the shelf life and efficacy of said composition.

6. A composition for preventing and treating dental disease by reducing the number of streptococcus sanguis bacteria in the mouth, said composition comprising a non sudsing dentifrice, wherein the dentifrice contains stabilized chlorine dioxide in a concentration in the range of between about 0.005%–0.5% and a phosphate compound selected from the group consisting of disodium hydrogen phosphate, sodium dihydrogen phosphate, and trisodium phosphate in a concentration in the range of between about 0.02%–3.0% to retard escape of chlorine dioxide from said composition at a pH in the range of 6.0 to 7.4, thereby increasing the shelf life and efficacy of said composition.

7. A composition for preventing and treating dental disease by reducing the number of streptococcus sanguis bacteria in the mouth, said composition comprising a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard the escape of chlorine dioxide from said composition at a pH in the range of 6.0 to 7.4, thereby increasing the shelf life and efficacy of said composition.

8. A composition for preventing and treating dental disease by reducing the number of yeasts including candida albicans in the mouth, said composition comprising a non sudsing dentifrice, wherein the dentifrice contains stabilized chlorine dioxide in a concentration range of between about 0.005%–0.5% and a phosphate compound selected from the group consisting of disodium hydrogen phosphate, sodium dihydrogen phosphate, and trisodium phosphate in a concentration in the range of between about 0.02%–3.0% to retard escape of chlorine dioxide from said composition at a pH in the range of 6.0 to 7.4, thereby increasing the shelf life and efficacy of said composition.

9. A composition for preventing and treating dental disease by reducing the number of yeasts including candida albicans in the mouth, said composition comprising a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard the escape of chlorine dioxide from said composition at a pH in the range of 6.0 to 7.4, thereby increasing the shelf life and efficacy of said composition.

10. A method for preventing and treating dental disease by reducing the number of bacteria in the mouth, said method comprising the step of applying a non sudsing dentifrice, wherein the dentifrice contains stabilized chlorine dioxide in a concentration in the range of between about 0.005%–0.5% and a phosphate compound selected from the group consisting of disodium hydrogen phosphate, sodium dihydrogen phosphate, and trisodium phosphate in a concentration in the range of between about 0.02%–3.0% to retard the escape of chlorine dioxide from the composition at a pH in the range of 6.0 to 7.4, thereby increasing the shelf life and efficacy of the composition.

11. The method as set forth in claim 10 wherein the concentration of stabilized chlorine dioxide is approximately 0.2% and the concentration of phosphate is approximately 1.0%.

12. A method for preventing and treating dental disease by reducing the number of bacteria in the mouth, said method comprising the step of applying a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard the escape of chlorine dioxide from the composition at a pH in the range 6.0 to 7.4, thereby increasing the shelf life and efficacy of the composition.

13. A method for preventing and treating dental disease by reducing the number of streptococcus mutans bacteria in the mouth, said method comprising the step of applying a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard the escape of chlorine dioxide from the composition at a pH in the range of 6.0 to 7.4, thereby increasing the shelf life and efficacy of the composition.

14. A method for preventing and treating dental disease by reducing the number of streptococcus sanguis bacteria in the mouth, said method comprising the step of applying a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard the escape of chlorine dioxide from the composition at a pH in the range of 6.0 to 7.4, thereby increasing the shelf life and efficacy of the composition.

15. A method for preventing and treating dental disease by reducing the number of yeasts including candida albicans in the mouth, said method comprising the step of applying a non sudsing dentifrice, wherein the dentifrice contains at least 0.1% stabilized chlorine dioxide and at least 0.05% of a phosphate compound selected from the group consisting of disodium hydrogen phosphate, sodium dihydrogen phosphate, and trisodium phosphate to retard the escape of chlorine dioxide from the composition at a pH in the range of 6.0 to 7.4, thereby increasing the shelf life and efficacy of the composition.

* * * * *